United States Patent [19]
Yamada et al.

[11] Patent Number: 5,643,911
[45] Date of Patent: Jul. 1, 1997

[54] MEDICAMENT FOR THERAPEUTIC AND PROPHYLACTIC TREATMENT OF DISEASES CAUSED BY SMOOTH MUSCLE CELL HYPERPLASIA

[75] Inventors: Kumi Yamada; Yoshikuni Tamao; Masahiro Ohshima; Norimichi Iwase, all of Yokohama, Japan

[73] Assignee: Mitsubishi Chemical Corporation, Tokyo, Japan

[21] Appl. No.: 441,743

[22] Filed: May 16, 1995

[30] Foreign Application Priority Data

May 19, 1994 [JP] Japan ............... 6-105367

[51] Int. Cl.⁶ .................................. A61K 31/495
[52] U.S. Cl. .............................. 514/254; 514/248
[58] Field of Search ................... 514/254, 248

[56] References Cited

FOREIGN PATENT DOCUMENTS 449203  8/1992  European Pat. Off. ............... 514/254

*Primary Examiner*—Marianne M. Cintins
*Assistant Examiner*—Keith MacMillan
*Attorney, Agent, or Firm*—Wenderoth, Lind & Ponack

[57] ABSTRACT

A method is provided for treating a disease caused by smooth muscle cell hyperplasia. According to this method, there is administered to a patient suffering from said disease a therapeutically or prophylactically effective amount of an aminopyridazine derivative or a salt thereof represented by the formula:

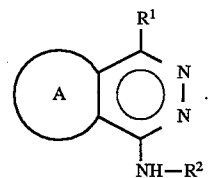

10 Claims, No Drawings

MEDICAMENT FOR THERAPEUTIC AND PROPHYLACTIC TREATMENT OF DISEASES CAUSED BY SMOOTH MUSCLE CELL HYPERPLASIA

BACKGROUND OF THE INVENTION

1. Field of the Invention

The present invention relates to medicaments for the therapeutic and prophylactic treatments of diseases caused by smooth muscle cell hyperplasia. More specifically, it relates to medicaments for the therapeutic and prophylactic treatments of diseases caused by smooth muscle cell hyperplasia which comprise as active ingredients specific aminopyridazine derivatives and salts thereof.

2. Related Art

Percutaneous transluminal coronary angioplasty (PTCA) and percutaneous transluminal angioplasty (PTA) have recently been widespread as methods for surgical treatments of constricted blood vessels. These methods comprise the steps of remotely inserting a balloon-catheter from femoral arteries or the like, and inflating the balloon at a constricted site to physically expand the vessel. However, restenosis are sometimes observed from 3 to 6 months after operations according to these treatments. In the restenosis, no deposition of cholesterol can be observed, while there is observed so-called cellular fibrous intimal hyperplasia predominantly consisting of smooth muscle cells and intercellular matrixes produced by these cells (Journal of American College of Cardiology, Vol. 23(6), pp.1278–1288, 1994, May). Furthermore, stenosis after the implantation of organs, e.g. heart, liver, kidney and vessels, is also caused by smooth muscle cell hyperplasia (FASEB Journal Vol. 7, pp.1055–1060, 1993, August).

Therefore, it is expected to be effective to inhibit migration and proliferation of smooth muscle cells generated in intravascular lumens for the therapeutic and prophylactic treatments of restenosis after the PTCA and PTA operations and stenosis after the implantation of organs.

In order to achieve the foregoing objects, researches on new drugs have been conducted [see, for example, Japanese Patent Unexamined Publication (KOKAI) Nos.(Sho)57-38715/1982, (Hei)2-121922/1990, (Hei)3-83923/1991, (Hei)3-83957/1991, (Hei)3-118383/1991, (Hei)4-99775/1992, and (Hei)4-154720/1992]. However, they have not been clinically developed so far.

It has been reported that various types of phthalazine derivatives have a wide variety of pharmacological activities. For example, as compounds having potent inhibitory activities in vivo on platelet aggregation, Japanese Patent Unexamined Publication (KOKAI) Nos.(Sho)56-53659/1981, (Sho)56-53660/1981, and (Sho)57-48972/1982 disclose 1-anilino-4-phenylphthalazine derivatives, and (Sho) 60-218377/1985 and (Sho)60-243074/1985 disclose compounds represented by the following formulas.

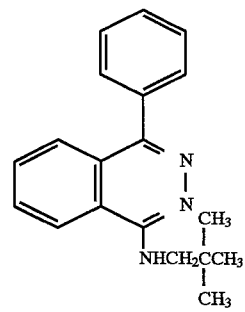

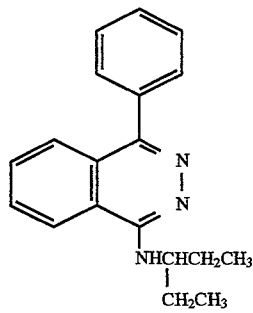

As to 1-amino-4-phenylphthalazine derivatives disclosed in British Patent No. 1303061 and Journal of Medicinal Chemistry (J. Med. Chem.), 12, 555 (1969), their anti-inflammatory and antirheumatic activities are solely described in the references.

In addition, European Patent Publication No.449203 A1 (corresponding to JP KOKAI (Hei)4-211666/1992) discloses 1-α-substituted-benzylamino-4-phenylphthalazine derivatives, and European Patent Publication No.534443 A1 discloses 3,6-di-substituted-pyridazine derivatives. It is disclosed that both of them have potent inhibitory activities on platelet aggregation, and that they can be expected to have efficacy on cerebrovascular diseases such as cerebral thrombosis and brain embolism, ischemic heart diseases such as cardiac infarction, and circulatory disorders such as peripheral circulatory disturbance based on their activities.

However, it has not been known that these phthalazine compounds have inhibitory activities on smooth muscle cell hyperplasia.

SUMMARY OF THE INVENTION

The present inventors conducted various researches to achieve the foregoing objects, and as a result, they first found that the aminopyridazine derivatives, known to have inhibitory activities on platelet aggregation, exhibit inhibitory activities on hyperplasia of smooth muscle cells generated in intravascular lumens. The present invention was achieved on the basis of these findings.

The present invention thus provides a medicament for the therapeutic and prophylactic treatment of a disease caused by smooth muscle cell hyperplasia which comprises as an active ingredient an aminopyridazine derivative or a salt thereof represented by the following Formula (I):

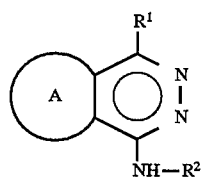
(I)

wherein $R^1$ represents cyclohexyl group; phenyl group which may be substituted with one or more substituents selected from the group consisting of $C_1-C_4$ alkyl groups, $C_1-C_4$ alkoxy groups and halogen atoms; thienyl group which may be substituted with one or more substituents selected from the group consisting of $C_1-C_4$ alkyl groups, $C_1-C_4$ alkoxy groups and halogen atoms; or furyl group which may be substituted with one or more substituents selected from the group consisting of $C_1-C_4$ alkyl groups, $C_1-C_4$ alkoxy groups and halogen atoms; $R^2$ represents —$CHR^3R^4$ wherein $R^3$ represents a hydrogen atom or a $C_1-C_4$ alkyl group and $R^4$ represents a $C_1-C_4$ alkyl group, cyclohexyl group, thienyl group, or phenyl group which may be substituted with one or more substituents selected from the group consisting of $C_1-C_4$ alkyl groups, $C_1-C_4$ alkoxy groups and halogen atoms; or $R^2$ represents cyclohexyl group which may be substituted with one or more substituents selected form the group consisting of $C_1-C_4$ alkyl groups, $C_1-C_4$ alkoxy groups and $C_1-C_6$ alkylene groups; and ring A represents a benzene ring, a thiophene ring or a furan ring.

According to the present invention, there are also provided a method for treating a disease caused by smooth muscle cell hyperplasia which comprises a step of administering to a patient suffering from the above mentioned disease a therapeutically or prophylactically effective amount of the aminopyridazine derivative or a salt thereof represented by the aforementioned Formula (I); and a use of the aminopyridazine derivative or a salt thereof represented by the aforementioned Formula (I) for the manufacture of a pharmaceutical composition for the therapeutic and prophylactic treatment of the disease caused by smooth muscle cell hyperplasia which comprises said aminopyridazine derivative or the salt thereof as an active ingredient and a pharmaceutically acceptable carrier or coating.

DETAILED EXPLANATION OF PREFERRED EMBODIMENTS

The present invention will be specifically explained below.

The medicament for the therapeutic and prophylactic treatment of the disease caused by smooth muscle cell hyperplasia according to the present invention comprises the aminopyridazine derivatives of the aforementioned Formula (I) or the salts thereof as an active ingredient.

In Formula (I), examples of the $C_1-C_4$ alkyl group include methyl group, ethyl group, n-propyl group, i-propyl group, n-butyl group, and t-butyl group; examples of the $C_1-C_4$ alkoxy group include methoxy group, ethoxy group, n-propoxy group, i-propoxy group, n-butoxy group, and t-butoxy group; and examples of the halogen atom include fluorine atom, chlorine atom, and bromine atom. Examples of the $C_1-C_6$ alkylene group include methylene group, ethylene group, trimethylene group, tetramethylene group, pentamethylene group, propylene group, ethylethylene group, and dimethylethylene group, which are formed by a combination of any two substituents.

As $R^1$, phenyl group, 2-thienyl group, or 2-furyl group are preferred, and phenyl group is particularly preferred. As $R^2$, —$CHR^{3,}R^{4,}$ wherein $R^{3,}$ represents a $C_1-C_4$ alkyl group and $R^{4,}$ represents a cyclohexyl group is preferred. 1-Cyclohexylethyl group is particularly preferred. Compounds wherein ring A represent benzene ring or thiophene ring, particularly benzene ring, are preferred.

Examples of the salts formed by the aminopyridazine derivatives of Formula (I) include inorganic acid addition salts such as, for example, hydrochloride, hydrobromide, hydriodide, sulfate, and phosphate; and organic acid addition salts such as, for example, methanesulfonate, p-toluenesulfonate, benzenesulfonate, camphorsulfonate, acetate, benzoate, malate, lactate, glyconate, glucuronate, maleate, fumarate, oxalate, ascorbate, citrate, salicylate, nicotinate, and tartarate. The compounds of Formula (I) and their salts may exist in the forms of hydrates or solvates, and accordingly, those hydrates and solvates also fall within the scope of the compounds according to the present invention.

Furthermore, where the aminopyridazine derivatives of Formula (I) have one or more asymmetric carbon atoms, the atoms may have any one of (R)-, (S)- and (RS)-configurations. Any of isomers derived therefrom falls within the scope of the compounds useful as active ingredients of the medicament according to the present invention.

Examples of the diseases caused by smooth muscle cell hyperplasia include, specifically, post-PTCA operative restenosis, stenosis after transplantation of organs, e.g. heart, liver, kidney, and vessels, and post-PTA operative restenosis.

Specific examples of the aminopyridazine compounds useful as the active ingredients of the medicament of the present invention are shown in Table 1 set out below.

TABLE 1

| Compound No. | $R^1$ | $R^2$ | A |
|---|---|---|---|
| 1 | —⟨H⟩ | —CH(CH₃)—⟨⟩ | ⟨⟩ |
| 2 | —⟨H⟩ | —CH(C₂H₅)—⟨⟩ | ⟨⟩ |
| 3 | —⟨H⟩ | —CH(CH₃)—⟨H⟩ | ⟨⟩ |
| 4 | —⟨H⟩ | —⟨H⟩ | ⟨⟩ |
| 5 | —⟨H⟩ | —⟨⟩ | ⟨⟩ |

TABLE 1-continued

Structure: A fused bicyclic ring system with ring A, substituent R¹, two N atoms, and NH-R²

| Compound No. | R¹ | R² | A |
|---|---|---|---|
| 6 | H | -CH(CH₃)-C₄H₉ⁿ | cyclohexyl |
| 7 | phenyl | -CH(CH₃)-phenyl | cyclohexyl |
| 8 | phenyl | -CH(C₂H₅)-phenyl | cyclohexyl |
| 9 | phenyl | -CH(C₄H₉ᵗ)-phenyl | cyclohexyl |
| 10 | 2-methylphenyl | -CH(CH₃)-phenyl | cyclohexyl |
| 11 | 2-chlorophenyl | -CH(CH₃)-phenyl | cyclohexyl |
| 12 | phenyl | -CH(CH₃)-(4-methylphenyl) | cyclohexyl |
| 13 | phenyl | -CH(CH₃)-(3-methylphenyl) | cyclohexyl |
| 14 | phenyl | -CH(CH₃)-(2-methylphenyl) | cyclohexyl |
| 15 | phenyl | -CH(CH₃)-(2-methoxyphenyl) | cyclohexyl |
| 16 | phenyl | -CH(CH₃)-(2-fluorophenyl) | phenyl |
| 17 | phenyl | -CH(CH₃)-cyclohexyl (H) | phenyl |
| 18 | phenyl | -CH(C₂H₅)-cyclohexyl (H) | phenyl |
| 19 | phenyl | -CH(C₃H₇ⁿ)-cyclohexyl (H) | phenyl |
| 20 | 2-methylphenyl | -CH(CH₃)-cyclohexyl (H) | phenyl |
| 21 | phenyl | -CH(CH₃)-thienyl (S) | phenyl |
| 22 | phenyl | -CH(CH₃)-phenyl | thienyl (S) |
| 23 | phenyl | -CH(CH₃)-cyclohexyl (H) | thienyl (S) |
| 24 | phenyl | cyclohexyl (H) | thienyl (S) |
| 25 | phenyl | adamantyl/bicyclic | thienyl (S) |
| 26 | phenyl | -CH(CH₃)-phenyl | thienyl (S) |

TABLE 1-continued

[Structure: Ring A fused with pyridazine bearing R¹ and NH—R²]

| Compound No. | R¹ | R² | A |
|---|---|---|---|
| 27 | phenyl | —CH(CH₃)—cyclohexyl | thiophene |
| 28 | phenyl | —CH(CH₃)—phenyl | furan |
| 29 | phenyl | —CH(CH₃)—cyclohexyl | furan |
| 30 | thienyl | —CH(CH₃)—phenyl | phenyl |
| 31 | thienyl | —CH(C₂H₅)—phenyl | phenyl |
| 32 | thienyl | —CH(CH₃)—cyclohexyl | phenyl |
| 33 | thienyl | 2-methylcyclohexyl | phenyl |
| 34 | thienyl | 2,3-dimethylcyclohexyl | phenyl |
| 35 | thienyl | —CH(CH₃)—C₂H₅ | phenyl |
| 36 | thienyl | —CH(CH₃)—C₃H₇ⁿ | phenyl |
| 37 | thienyl | —CH(CH₃)—C₃H₇ⁱ | phenyl |
| 38 | thienyl | —CH(CH₃)—CH₂CH(CH₃)₂ | phenyl |
| 39 | thienyl | —CH(C₂H₅)—C₂H₅ | phenyl |
| 40 | thienyl | —CH₂C₄H₉ᵗ | phenyl |
| 41 | 3-methylthienyl | —CH(CH₃)—phenyl | phenyl |
| 42 | 3-methylthienyl | —CH(CH₃)—cyclohexyl | phenyl |
| 43 | thienyl (isomer) | —CH(CH₃)—phenyl | phenyl |
| 44 | thienyl (isomer) | —CH(C₂H₅)—phenyl | phenyl |
| 45 | thienyl (isomer) | —CH(CH₃)—cyclohexyl | phenyl |
| 46 | furyl | —CH(CH₃)—phenyl | phenyl |
| 47 | furyl | —CH(CH₃)—cyclohexyl | phenyl |

The aforementioned aminopyridazine derivatives are compounds described in European Patent Publication Nos. 449203 A1 and 534443 A1, and each of the compounds can be prepared according to the methods described in the patent documents.

The medicament of the present invention for the therapeutic and prophylactic treatments of diseases caused by smooth muscle cell hyperplasia have efficacy on various diseases caused by migration and hyperplasia of smooth muscle cells generated in intravascular lumens. More specifically, they can be used for the therapeutic and prophylactic treatments of post-PTCA (percutaneous transluminal coronary angioplasty) operative restenosis, post-PTA (percutaneous transluminal angioplasty) operative restenosis, stenosis after the transplantation of organs such as heart, liver, kidney and vessels.

According to one embodiment of the present invention, the method for treating the above-described diseases is provided, which comprises a step of administering to a patient suffering from such disease an therapeutically or prophylactically effective amount of the aminopyridazine derivative or the salt thereof.

Where the aforementioned aminopyridazine derivatives are clinically used as medicament for the therapeutic and prophylactic treatments of diseases caused by smooth muscle cell hyperplasia, it is preferable that a single dose of 1 to 200 mg is orally administered to an adult patient once to 3 times a day, or a single dose of 0.01 to 10 mg is administered to an adult patient by intravenous injection once to 5 times a day or a dose of 0.01 to 50 mg a day is administered to an adult patient by infusion. For intrarectal administration, a single dose of 1 to 100 mg is preferably administered once to 3 times a day. More preferably, above-mentioned doses may be suitably increased or decreased depending on the age, pathology, and conditions of a patient to be treated.

According to another embodiment of the present invention, there is provided a use of the above-mentioned aminopyridazine derivative or the salt thereof for the manufacture of the medicament in a form of a pharmaceutical composition for the therapeutic and prophylactic treatment of the disease caused by smooth muscle cell hyperplasia which comprises the above-described aminopyridazine derivative or the salt thereof as an active ingredient and a pharmaceutically acceptable carrier or coating.

For formulating the pharmaceutical composition, one or more of the aminopyridazine derivatives or pharmacologically acceptable salts thereof may be mixed with ordinarily used pharmaceutical carriers or coatings, e.g. excipients or other additives. The carrier may be either solid or liquid. Examples of the solid carriers include lactose, Bolus alba (kaolin), saccharose, crystalline cellulose, corn starch, talc, agar, pectin, acacia, stearic acid, magnesium stearate, lecithin, and sodium chloride.

Examples of the liquid carriers include syrup, glycerin, peanut oil, polyvinyl pyrrolidone, olive oil, ethanol, benzyl alcohol, propylene glycol, and water. The pharmaceutical composition of the present invention may be formulated in any one of various forms. Where solid carriers are used, the medicament may be formulated in a form of, for example, tablets, powder, granules, hard gelatin capsules, suppositories, or troches. The amount of the solid carrier may preferably be from about 1 mg to about 1 g, however, the amount may widely vary and is not limited within the above range. Where liquid carriers are used, formulations may be, for example, in a form of syrups, lotions, soft gelatin capsules, sterile injections contained in ampoules or the like, or aqueous or non-aqueous suspensions.

EXAMPLES

The present invention will be further explained by way of examples. However, the scope of the present invention is defined only by the appended claims and not limited to the following examples.

Preparative Example

Synthesis of the fumarate of (R)-1-(1-cyclohexylethylamino)-4-phenylphthalazine (Compound No. 17 in Table 1 in R-configuration, hereinafter referred to as "Compound A")

To 400 ml of N-methylpyrrolidone, 144.4 g (0.6 mol) of 1-chloro-4-phenylphthalazine and 230 g (1.8 mol) of (R)-(−)-1-cyclohexylethylamine were added, and the mixture was heated to 120° to 130° C. for 6 hours with stirring. After completion of the reaction, the mixture was cooled and added with 4.0 l of 5% aqueous NaOH solution, and then extracted with chloroform. The organic layer was dried over $MgSO_4$, concentrated and purified by silica gel column chromatography (eluent; ethyl acetate/hexane/chloroform= 1:3:1). After recrystallization from ether/chloroform, 150.2 g of (R)-1-(1-cyclohexylethylamino)-4-phenylphthalazine was obtained. m.p. 164.0°–167.0° C.

To 1 l of methanol, 100 g of the above-obtained (R)-1-(1-cyclohexylethylamino)-4-phenylphthalazine and 32.0 g of fumaric acid were added and the mixture was refluxed for 16 hours with stirring. The mixture was allowed to stand and cool to 20° C. with stirring. Crystals were collected by filtration, washed with 200 ml of methanol, and then dried at about 60° C. under 1–2 mmHg to afford 121.5 g of fumarate. m.p. 240°–250° C. (decomposition).

Example 1

Effect on Rat Intimal Hyperplasia Model

Male SD rats (20 weeks old) anesthetized with pentobarbital were fixed in dorsal position and its left carotid artery was exposed. A Fogarty 2 French balloon catheter was inserted through the external carotid artery to the bifurcation of aorta (about 5 cm). Then, the balloon was inflated and the catheter was pulled back to the inserted site with rotation. This procedure was repeated 3 times to remove endothelial cells of the carotid artery. After the procedures were completed, the catheter was drawn out, and then the external carotid artery was ligated and the incisional site was closed with a medical clip. Compound A was suspended in a 0.7% tragacanth solution and orally administered once a day in an amount of 1 mg/kg, 3 mg/kg or 10 mg/kg. Control animals were administered orally in a similar manner with 0.7% tragacanth solution. The administration of the first day was carried out immediately after balloon injury.

Two weeks after balloon injury, 3% Evans blue was intravenously administered through the femoral vein to the rat anesthetized with pentobarbital. After thirty minutes, the rat was subjected to celiotomy and its whole body was perfused with 0.01M phosphate buffer in the abdominal aorta. Then, the carotid artery was removed.

A portion of the removed carotid artery, where the removal of endothelial cells was observed, was cut into 6 to 8 artery fragments with a length of 2 mm, which were then fixed with formalin and embedded in paraffin. Cross-sectional tissue slices were prepared from each of the blocks and then the slices were stained by the Elastica-van Gieson method. Intimal and medial areas of each slice were determined by a digitizer, and degrees of intimal hyperplasia were represented by ratios of intimal area/medial area. Results are shown in Table 2.

Compound A dose-dependently inhibited the intimal hyperplasia in rat carotid arteries induced by removal of intima.

TABLE 2

| | Dose | Numbers of animals | Ratio of intima/media mean ± S.E. |
|---|---|---|---|
| Control | — | 14 | 1.060 ± 0.081 |
| Compound A | 1 mg/kg | 7 | 0.853 ± 0.107 |

TABLE 2-continued

| | Dose | Numbers of animals | Ratio of intima/media mean ± S.E. |
|---|---|---|---|
| Compound A | 3 mg/kg | 8 | 0.637 ± 0.067※ |
| Compound A | 10 mg/kg | 9 | 0.462 ± 0.094※ |

※p < 0.05, One-way analysis of variance (Dunnett test)

Example 2

Effect on Rat Intimal Hyperplasia Model

Male SD rats (20 weeks old) anesthetized with pentobarbital were fixed in dorsal position and the left carotid artery was exposed. A Fogarty 2 French balloon catheter was inserted from the external carotid artery to the bifurcation of aorta (about 5 cm). Then, the balloon was inflated and the catheter was pulled back to the inserted site with rotation. This procedure was repeated 3 times to remove endothelial cells of the carotid artery. After the procedures were completed, the catheter was drawn out, and then the external carotid artery was ligated and the incisional site was closed with a medical clip. Compound A was suspended in a 0.7% tragacanth solution and orally administered once a day in an amount of 3 mg/kg, and control animals were administered orally in a similar manner with 0.7% tragacanth solution. For Group A, the first administration was carried out immediately after the removal of intima of the carotid artery. For Group B, administration was started four days after balloon injury.

Two weeks after balloon injury, 3% Evans blue was intravenously administered through the femoral vein to the rat anesthetized with pentobarbital. After thirty minutes, the rat was subjected to celiotomy and its whole body was perfused with 0.01M phosphate buffer in the abdominal aorta. Then, the carotid artery was removed.

The portion of the removed carotid artery where the removal of endothelial cells was observed was cut into 6 to 8 artery fragments with a length of 2 mm, which were then fixed with formalin and embedded in paraffin. Cross-sectional tissue slices were prepared from each of the blocks and the slices were stained by the Elastica-van Gieson method. Intimal and medial areas of each slice were determined by a digitizer, and degrees of intimal hyperplasia were represented by ratios of intimal area/medial area. Results are shown in Table 3.

Compound A inhibited the subendothelial hyperplasia in rat carotid arteries induced by removal of intima by oral administration at the dose of 3 mg/kg. The administration started 4 days after the removal of intima also found to be significantly effective.

TABLE 3

| | Administration period (day) | Numbers of animals | Ratio of intima/media mean ± S.E. |
|---|---|---|---|
| Control | — | 7 | 1.033 ± 0.086 |
| Compound A | A 0–14 | 6 | 0.568 ± 0.037※ |
| Compound A | B 4–14 | 6 | 0.594 ± 0.044※ |

P < 0.05, One-way analysis of variance (Dunnett test)

The above-described aminopyridazine derivatives inhibit migration and hyperplasia of smooth muscle cells. Accordingly, they are useful for the therapeutic and prophylactic treatments of diseases caused by smooth muscle cell hyperplasia, e.g., post-PTCA (percutaneous transluminal coronary angioplasty) operative restenosis, stenosis after transplantation of organs such as heart, liver, kidney and vessels, and post-PTA (percutaneous transluminal angioplasty) operative restenosis.

What is claimed is:

1. A method for treating smooth muscle cell hyperplasia which comprises a step of administering to a patient in need of such treatment an therapeutically or prophylactically effective amount of an aminopyridazine derivative or a salt thereof represented by the following Formula (I):

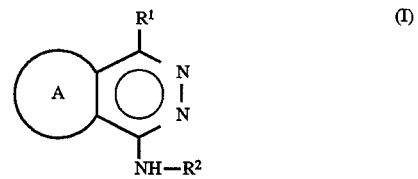

wherein $R^1$ represents cyclohexyl group; phenyl group which may be substituted with one or more substituents selected from the group consisting of $C_1$–$C_4$ alkyl groups, $C_1$–$C_4$ alkoxy groups and halogen atoms; thienyl group which may be substituted with one or more substituents selected from the group consisting of $C_1$–$C_4$ alkyl groups, $C_1$–$C_4$ alkoxy groups and halogen atoms; or furyl group which may be substituted with one or more substituents selected from the group consisting of $C_1$–$C_4$ alkyl groups, $C_1$–$C_4$ alkoxy groups and halogen atoms; $R^2$ represents —$CHR^3R^4$ wherein $R^3$ represents a hydrogen atom or a $C_1$–$C_4$ alkyl group and $R^4$ represents a $C_1$–$C_4$ alkyl group, cyclohexyl group, thienyl group, or phenyl group which may be substituted with one or more substituents selected from the group consisting of $C_1$–$C_4$ alkyl groups, $C_1$–$C_4$ alkoxy groups and halogen atoms; or $R^2$ represents a cyclohexyl group which may be substituted with one or more substituents selected form the group consisting of $C_1$–$C_4$ alkyl groups, $C_1$–$C_4$ alkoxy groups and $C_1$–$C_6$ alkylene groups; and ring A represents a benzene ring, a thiophene ring or a furan ring.

2. The method according to claim 1, wherein $R^2$ represents —$CHR^3R^4$ in which $R^3$ represents a $C_1$–$C_4$ alkyl group and $R^4$ represents cyclohexyl group.

3. The method according to claim 1, wherein $R^1$ represents phenyl group, 2-thienyl group, or 2-furyl group.

4. The method according to claim 1, wherein $R^1$ represents phenyl group.

5. The method according to claim 1, wherein the ring A represents a benzene ring or a thiophene ring.

6. The method according to claim 1, wherein the ring A represents a benzene ring.

7. The method according to claim 1, wherein $R^1$ represents phenyl group, $R^2$ represents 1-cyclohexylethyl and the ring A represents a benzene ring.

8. The method according to claim 1, wherein the treatment is of a disease selected from the group consisting of post-percutaneous transluminal coronary angioplasty operative restenosis, stenosis after transplantation of organs, and post-percutaneous transluminal angioplasty operative restenosis.

9. A method for treating smooth muscle cell hyperplasia which comprises a step of administering to a patient in need of such treatment an therapeutically or prophylactically effective amount of (R)-1-(cyclohexylethylamino)-4-phenylphthalazine or a pharmaceutically acceptable salt thereof.

10. The method according to claim 9, wherein the treatment is of a disease selected from the group consisting of post-percutaneous transluminal coronary angioplasty operative restenosis, stenosis after transplantation of organs, and post-percutaneous transluminal angioplasty operative restenosis.

* * * * *